United States Patent [19]

Allegra et al.

[11] Patent Number: 4,694,007

[45] Date of Patent: Sep. 15, 1987

[54] USE OF TRIMETREXATE AS ANTIPARASITIC AGENT

[75] Inventors: Carmen Allegra, Vienna, Va.; James C. Drake, Ijamsville, Md.; Bruce A. Chabner, Potomac, Md.; Henry Masur; Joseph A. Kovacs, both of Bethesda, Md.

[73] Assignee: The United States of America as represented by the Secretary of the Department of Health and Human Services, Washington, D.C.

[21] Appl. No.: 865,055

[22] Filed: May 20, 1986

[51] Int. Cl.$^4$ ........................................... A61K 31/505
[52] U.S. Cl. .................................................... 514/260
[58] Field of Search ......................................... 514/260

[56] References Cited

U.S. PATENT DOCUMENTS 4,376,858  3/1983  Colbry .............................. 544/291
4,391,809  7/1983  Elslager ............................. 514/260

OTHER PUBLICATIONS

The Merck Index, 9th Ed., Merck & Co., Inc., Rahway, N.J., 1976, p. 544, No. 4086.

Primary Examiner—Jerome D. Goldberg
Attorney, Agent, or Firm—Browdy and Neimark

[57] ABSTRACT

A method of treating infections of Toxoplasmosis or *P. carini* comprising administering to the host an effective amount of trimetrexate, (2,4-diamino-5-methyl-6-[(3,4,5-trimethoxyanilino)methyl]quinazoline.

5 Claims, 3 Drawing Figures

USE OF TRIMETREXATE AS ANTIPARASITIC AGENT

FIELD OF THE INVENTION

The present invention relates to the use of the antifolate trimetrexate as an antiparasitic agent, specifically for use in treating infections from *Toxoplasma gondii* and *Pneumocistis carinii*.

BACKGROUND OF THE INVENTION

*Toxoplasma gondii* is a common protozoan infection in man, with a sero-positivity in 30-50% of North Americans. Life-threatening toxoplasmosis occurs most often in patients with defective cell-mediated immunity who appear to reactivate previously acquired infection and develop severe encephalitis or disseminated disease. Life-threatening infections have occurred most often in organ-transplant recipients and patients with hematologic malignancies. More recently, toxoplasmosis has become a particularly prevalent opportunistic infection in patients with acquired immune deficiency syndrome (AIDS).

Systemic infection with toxoplasmosis and *Pneumocistis carinii* are generally treated with the antifolates pyrimethamine and trimethoprim, respectively. In the general population of patients with an intact immune system, these treatments have met with good success. However, over the past 3-4 years these infections have become widespread in the population of patients with AIDS. The AIDS syndrome develops following infection with a specific virus, HTLV-3, producing severe immune deficiency and increasing the risk of infection with opportunistic organisms such as *Toxoplasmosis* and *P. carinii*. Infection with these organisms in the AIDS population is extremely refractory to standard therapy, and many of those infected ultimately die from infectious complications. Therapy of *Pneumocistis carinii* pneumonia in the expanding population with AIDS has become problematic because of the high frequency of therapeutic failures. Because of the fastidious nature of the causative organisms, current treatment choices have been made with little information on the effects of the agents on the PC metabolic pathway.

Another problem encountered in treating patients with AIDS is the considerable number of patients (up to 60%) who develop allergic reactions or serious side effects during therapy with a sulfonamide and trimethoprim or pyrimethamine. No alternative regimen to sulfonamide and pyrimethamine has been found effective for the therapy of toxoplasma encephalitis.

Recently, the surge in the number of AIDS patients with toxoplasma encephalitis has highlighted the need for more effective therapies and for alternative drugs for those unable to tolerate pyrimethamine and sulfa drugs. Many AIDS patients develop life-threatening leukopenia, thrombocytopenia, hepatitis. or rash while receiving pyrimethamine and sulfa, yet no alternative regimen using these drugs singly or in combination with other drugs has been found to be effective.

*Pneumocistis carinii* (PC) pneumonia is the leading cause of death in the expanding population of patients with acquired immunodeficiency syndrome (AIDS). Current therapy for PC pneumonia consists of a dihydrofolate reductase inhibitor, most commonly the diaminopyrimidine trimethoprim, coupled with sulfa . . . oxazol, a dihydropteroate synthesis inhibitor. Presumably the synergistic interaction of these two compounds in the PC organism leads to folate depletion with resultant cessation of purine and thymidine synthesis and ultimately cell death.

Because of clinical resistance or drug intolerance, including allergic reactions and bone marrow suppression, approximately 40-60% of patients cannot be successfully treated. Because of the fastidious nature of this organism and its inability to grow in vitro, inhibition studies on key enzymes have been lacking. The choice of metabolic inhibitors used to treat PC pneumonia has been largely based on empiric data and the assumption that the DHFR in the causative organism is similar to bacteria and other protozoa in its sensitivity to the diaminopyrimidine inhibitors. While these inhibitors are apparently able to penetrate the cellular membrane of protozoa, there exists no data to allow a choice among the myriad available DHFR inhibitors. In contrast to these agents, highly potent DHFR inhibitors that retain the classic puridine structure such as methotrexate are ineffective in the treatment of bacterial and protozoal infections due to the lack of a specific membrane carrier required for the transport of these structures.

Dihydrofolate reductase (E.C.1.5.1.3;5,6,7,8-tetrahydrofolate:NADP+ oxoreductase) is required to maintain the intracellular pool of reduced folates in rapidly dividing cells. Inhibitors of this enzyme have proven effective in both antineoplastic and antimicrobial chemotherapy. Methotrexate, an analog that preserves the basic folate (pteroylglutamate) structure, potently inhibits dihyroreductase from mammalian and bacterial sources, but requires transport by a folate-specific membrane carrier found only on mammalian cells, and is therefore primarily useful as an antineoplastic agent. The diaminopyrimidines pyrimethamine and trimethaprim readily penetrate mammalian and microbial cells by diffusion, have intermediate inhibitory activity against bacterial dihydrofolate reductase but lesser potency against mammalian dihydrofolate reductase, and are used primarily in antibacterial and antiprotozoal therapy in combination with an inhibitor of folate synthesis such as sulfamethoxazole. While the diaminopyrimidines in combination with sulfonamides have become the primary form of therapy for certain parasitic infections, including toxoplasmosis, little is known concerning the transport of the various types of antifolates and the potency of their inhibition of dihydrofolate reductase in these organisms.

There is no current biochemical data addressing the ability of the currently used antifolates to inhibit the target enzyme, dihydrofolate reductase, in either toxoplasmosis or *P. Carinii*. Great variations exist in the ability of a given antifolate to inhibit the dihydrofolate reductase from different species. It has been speculated that pyrimethamine and trimethoprim are effective inhibitors of dihydrofolate reductase from these two organisms in a fashion similar to that observed in bacteria and plasmodia wherein the drugs are highly effective.

SUMMARY OF THE INVENTION

It is an object of the invention to overcome deficiencies in the prior art, such as mentioned above.

It is another object of the invention to provide for the improved treatment of opportunistic parasitic infections.

It is a further object of the invention to provide a new therapeutic use for trimetrexate, either alone or in combination with leucovorin.

It is still another object of the present invention to provide an antiparasitic agent for use in treating infections from *Toxoplasma gondii* and *Pneumocistis carinii*.

It has been found that dihydrofolate reductase (DHFR) from toxoplasmosis and *P. carinii* responds to antifolates in a manner more akin to enzyme from mammalian sources, which are extremely insensitive to inhibition by pyrimethamine and trimethoprim. However, it has been found that these enzymes are highly sensitive to inhibition by trimetrexate, a lipid soluble antifolate conventionally used to treat neoplastic diseases. Trimetrexate, 2,4-diamino-5-methyl-6-[(3,4,5-trimethoxyanilino)methyl]quinazoline, a known antitumor agent, has been found to be 1000-fold more potent an inhibitor of the catalytic activity of dihydrofolate reductase from *Toxoplasmosis gondii* when compared to conventional drugs. Because of its lipid solubility, trimetrexate is readily transported by this organism. Treatment of murine toxoplasmosis indicates that, in combination with the physiologic folate leucovorin (which is transported by mammalian but not by parasitic cells), trimetrexate is a potent and selective anti-parasitic drug which has no discernible toxicity for the mammalian host. The trimetrexate can be administered intraperitoneally for inhibition of the dihydrofolatereductase of the *T. gondii* or *P. carinii* parasites. Trimetrexate rapidly reaches high concentrations in the protozoa, which lack a transmembrane transport system for physiologic folates and for the classic antifolate used in cancer chemotherapy, methotrexate.

Treatment of mice infected with *T. gondii* with a combination of trimetrexate (30 mg/kg per day for nine days) and the reduced folate leucovorin (30 mg/kg per day for nine days) demonstrated that the toxic side effects of the antifolate could be abolished through use of the antidote while preserving a potent antiprotozoal effect.

The concentration required for 50% inhibition of protozoal DHFR was 1.4 nM. As an inhibitor of this enzyme, trimetrexate was found to be almost 600-fold more potent than pyrimethamine, the DHFR inhibitor currently used to treat toxoplasma infection.

When toxoplasmosis protozoan was incubated with 1 micromole trimetrexate, the drug rapidly reached high intracellular concentrations. Since toxoplasma organisms lack a transmembrane transport system for physiologic folates (and for the classic antifolate used in cancer chemotherapy, methotrexate), host toxicity can be prevented by co-administration of the reduced folate, leucovorin, without reducing the antiprotozoal effect.

The effectiveness of trimetrexate against toxoplasma was demonstrated both in vitro and in vivo. Proliferation of toxoplasma in murine microphages in vitro was completely inhibited by exposure of these cells to 10-7M trimetrexate for 18 hours. Treatment of *T. gondii* infected mice with a combination of trimetrexate (30 mg/kg per day for 9 days) and leucovorin (30 mg/kg per day for 9 days) extended survival of these animals by greater than 300% over control animals.

DETAILED DESCRIPTION OF THE INVENTION

Figure 1:
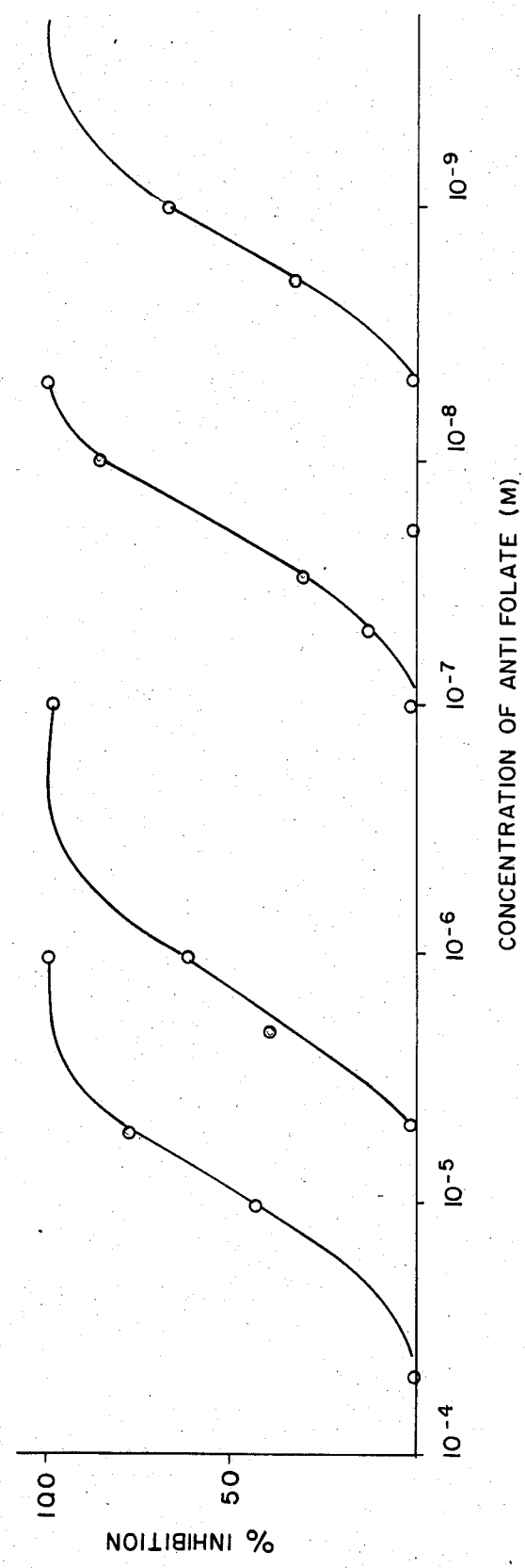
FIG. 1 shows the percent inhibition of catalytic activity of DHFR isolated from the *T. gondii* trophozoites with respect to the concentration of four antifolates using the experimental conditions detailed in Table I. The four antifolates used were trimethoprim (△—△), pyrimethamine (◇—◇), methotrexate (○—○) and trimetrexate (□—□).
Figure 2B:
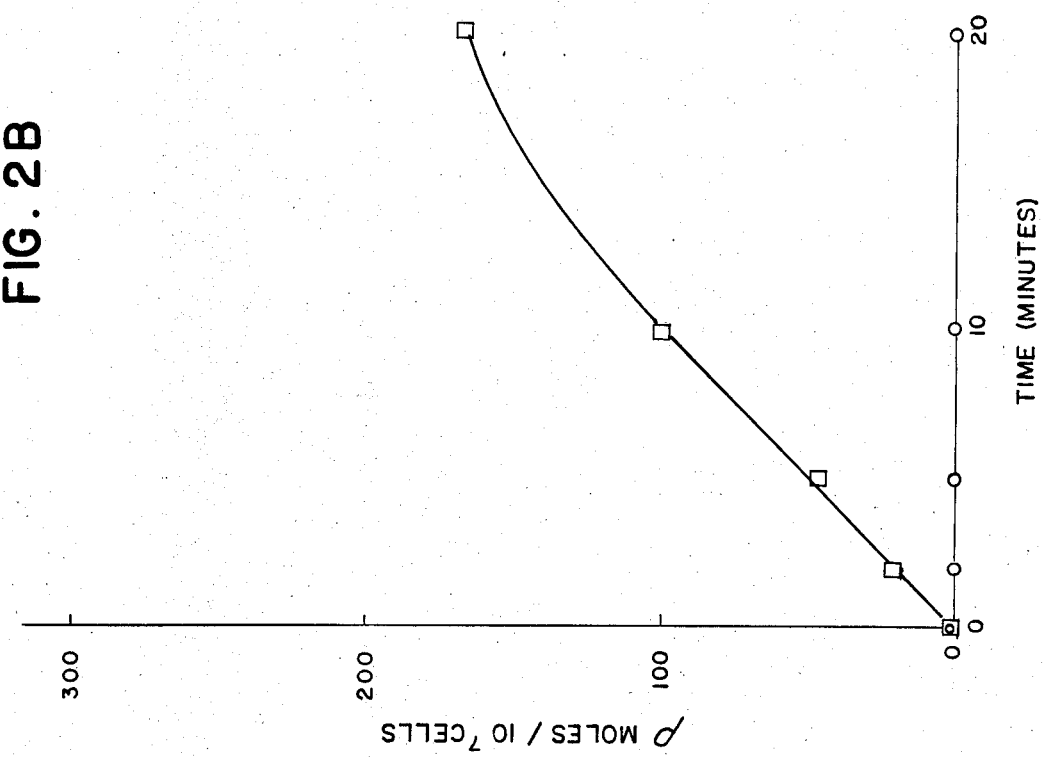
FIG. 2b shows the uptake of leucovorin by HL-60 cells (□—□) and *T. gondii* trophozoites (○—○).
Figure 2A:
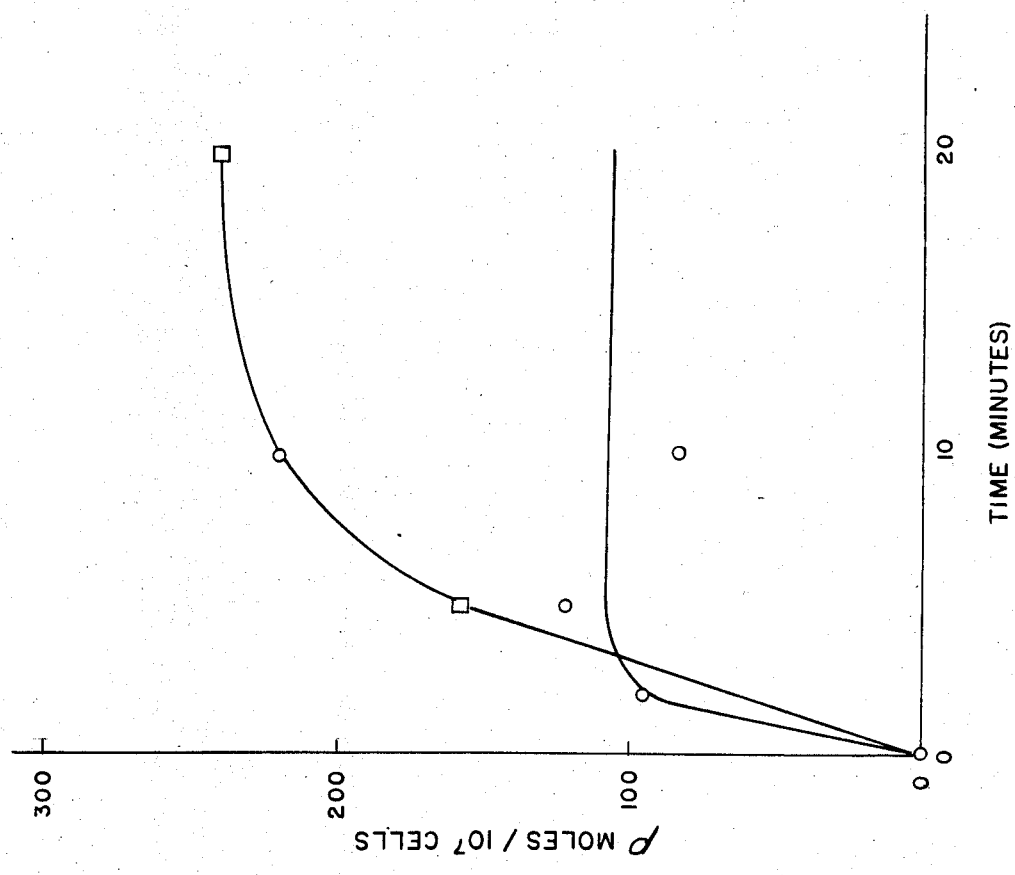
FIG. 2a shows the uptake of trimetrexate over time by human HL-60 cells (■—■) and *T. gondii* trophozoites (●—●).

To investigate the inhibitory effects of anitfolates, DHFR was extracted from toxoplasma trophozoites and was found to be stable in the presence of protease inhibitors leupeptin and chymostatin for at least a 48-hour period at 4° C. The specific activity of the toxoplasma DHFR in the cytosol preparation was $1.14 \pm 0.09$ nmoles/min/mg protein at 37° C. ($32 \pm 3 \times 10^6$ trophozoites/mg protein). The catalytic activity was found to be linear with time for greater than 10 minutes and with protein up to 1 mg or 0.0012 units of DHFR (1 unit=1 micro mole/min/mg). The binding of methotrexate to the enzyme was also found to be linear with respect to protein up to 0.7 mg. To determine whether the DHFR activity in suspensions of toxoplasma were influenced by adherent murine peritoneal macrophages (0.2% in purified solutions), DHFR activity was assayed in peritoneal macrophage preparations from normal or toxoplasma-infected mice such that the concentrations exceeded those found in the purified toxoplasma preparation by up to two fold ($13 \times 10^6$ peritoneal macrophages/ml.). No discernible activity in either the catalytic or the methotrexate binding assay was detected in these preparations.

In addition to toxoplasma DHFR, inhibition studies were conducted on DHFR isolated from three mammalian sources (human, rat, and bovine liver) and a bacterial source (*Lactobacillus casei*). For each source of reductase, inhibition studies were performed using the anti-folates pyrimethamine, trimethoprim, methotrexate, and trimetrexate. In each case, the inhibitory potential of the inhibitors was assessed by their ability to inhibit the catalytic reaction ($I_5$) and their ability to displace enzyme-bound [$^3$H]-methotrexate to yield a relative binding affinity with respect to methotrexate.

It was found that methotrexate and trimetrexate are potent inhibitors of reductase regardless of the source of the enzyme ($I_{50}=1-21$ nM). In contrast, trimethoprim is a poor inhibitor of mammalian reductase ($I_{50}=390,000-1,300,000$ nm) but is a potent inhibitor of bacterial reductase (280 nm). Pyrimethamine is 200- to 400-fold more potent an inhibitor of mammalian reductase when compared to trimethoprim, but it was a weak inhibitor of the DHFR from the bacterial source (7400 nM). Trimethoprim and pyrimethamine weakly inhibited the toxoplasma reductase with $I_{50}$'s of 14,500 and 760 nM, respectively, while methotrexate and trimetrexate were both extremely potent toxoplasma reductase inhibitors. In particular, trimetrexate is more than 500-fold more potent an inhibitor of toxoplasma reductase when compared to pyrimethane and 10,000-fold more potent than trimethaprim. Table I shows the binding affinities of the inhibitors relative to methotrexate. These values, expressed as DMTX, are the ratio of the amount of inhibitor required to displace 50% of the enzyme-bound methotrexate at a methotrexate concentration of 2 nm, and, as such, are a measure of the enzyme binding affinity of each inhibitor as compared to methotrexate, methotrexate being equal to 1. The binding affinities parallel and further support the kinetic studies that showed a marked potency of methotrexate and trimetrexate as inhibitors of DHFR from *T. gondii*.

and with up to 1 mg protein or 0.0012 units of DHFR (1 unit = 1 micromole/min/mg) per assay pf 1 ml total volume.

TABLE 1

COMPARATIVE INHIBITION OF DHFR BY ANTIFOLATES

| DHFR Source | Trimethoprim $I_{50}$ (nM) | ΔMTX | Pyrimethamine $I_{50}$ (nM) | ΔMTX | Trimetrexate $I_{50}$ (nM) | ΔMTX | Methotrexate $I_{50}$ (nM) | ΔMTX |
|---|---|---|---|---|---|---|---|---|
| Human | 1,300,000 ± 250,000[a] | 30,500 | 5,800 ± 1400 | 205 | 3.2 ± 0.64 | 1.6 | 1.2 ± 0.18 | 1 |
| Bovine | 400,000 ± 70,000 | 9,000 | 1,400 ± 330 | 43 | 14 ± 2.4 | 2.5 | 1.0 ± 0.14 | 1 |
| Rat | 390,000 ± 150,000 | 3,315 | 2,400 ± 860 | 145 | 5.7 ± 1.1 | 2.9 | 1.4 ± 0.48 | 1 |
| *L. casei* | 280 ± 70 | 45.5 | 7,400 ± 1100 | 6500 | 6.1 ± 1.1 | 6.0 | 1.8 ± 0.27 | 1 |
| Toxoplasma | 14,500 ± 1,900 | 900 | 760 ± 130 | 115 | 1.4 ± 0.16 | 0.3 | 21 ± 2.9 | 1 |

[a] = SEM

*T. Gondii* DHFR was isolated from the peritoneal exudate of BALB/c mice three days following an intraperitoneal inoculation of $5 \times 10^5$ *T. gondii* trophozoites. The exudate was suspended in phosphate-buffered saline and the toxoplasma trophozoites were separated from inflammatory cells by differential centrifugation as described by Jones et al. in *J. Exper. Med.* (1975) 141:466–482. The sedimented toxoplasma organisms were then resuspended in 1 ml of phosphate-buffered saline containing 50 microg/ml of each of the protease inhibitors chymostatin and leupeptin. The organisms were then disrupted with a 60-sec burst from a cell disrupted (Virsonic model 16-850) while at 4° C. The disrupted organisms were centrifuged at 20,000×g for 15 minutes, and the resulting supernatant was used as the source of dihydrofolate reductase. The number of organisms as well as residual contaminating peritoneal microphages were measured on all preparations prior to and following sonication. To determine whether the DHFR activity in suspensions of toxoplasma was influenced by contamination with adherent murine peritoneal macrophages (2 cells/100 trophozoites in purified preparations), DHFR activity was assayed in peritoneal macrophage preparations from normal mice using up to 2 mg protein per ml of assay. No discernible DHFR was detected in these preparations by either the catalytic or the methotrexate binding assay.

The catalytic activity of dihydrofolate reductase from various sources was assayed spectrophotometrically. Bovine liver DHFR (8 U/mg) and rat liver DHFR (3.7 U/mg) were obtained from Sigma Chemical Co., St. Louis, Mo. Human DHFR purified from a human breast cancer cell line (MCF-7) (27 U/mg) was a gift from Dr. Bernard Kaufman of the National Cancer Institute. *L. casei* reductase was obtained from the New England Enzyme Center of Boston, Mass. Each 1 ml sample and blank cuvette contained 0.15 umoles of NADPH in 160 mm Tris-HCl, pH 7.2, and 160 mm KCl with DHFR (sample cuvette only) and various concentrations of inhibitors. The samples were allowed to reach a temperature equilibrium at 37° cover a 10-minute period, and the reaction was initiated with the addition of 0.075 micromoles of dihydrofolic acid. The reaction velocity was measured with a Beckman Acta III dual-beam spectrophotometer by following the change in optical density at 340 nm. Changes in optical density were converted to molar quantities by using an extinction coefficient for the reaction of $6.01 \times 10^3$.

Enzyme activity was found to be stable in the presence of the protease inhibitors leupeptin and chymostatin for at least 48 hours at 4° C. The specific activity of the toxoplasma DHFR in the cytosol preparation was 1.14+0.09 nmoles/min/mg protein at 37° C. ($32 = 3 \times 10^6$ tropozoites/mg protein). The catalytic activity was linear with time for greater than 10 minutes The binding affinity of each of the inhibitors for the various reductases was determined relative to methotrexate (MTX) by measuring the capacity of each to displace enzyme-bound [$^3$H]-methotrexate (Moran '84). Each 450 ul assay contained 0.15 umole of NADPH, DHFR, 1 pmole of [$^3$H]-methotrexate (sp. act. = 18 Ci/mole), and various concentrations of competitors (inhibitors) in 50 mm $KH_2PO_4$, pH 7.4. The samples were allowed to reach an equilibrium over 10 minutes at 21° C. followed by adsorption of unbound labelled methotrexate with the addition of 50 microliters of an albumin-coated activated charcoal solution. The activated charcoal solution was prepared as follows: 100 gm of activated charcoal, 100 mg of bovine serum albumin, and 10 mg of high molecular weight dextran in 100 microliters of distilled water. Following the addition of charcoal, enzyme-bound [$^3$H]-methotrexate was separated from the charcoal by filtration. The separated enzyme-bound [$^3$H]-methotrexate was then dissolved in 10 microliters of scintillant (Ready-Solv, Beckman, Irvine, Calif.) and counted in a Searle Model III liquid scintillation counter.

The binding of methotrexate to DHFR from toxoplasma trophozoites was linear for protein concentrations up to 0.7 mg of supernate per ml in the final assay solution. The tabulated values were calculated using ALLFIT, a computer-assisted, least squares curve-fitting program. The program is based on the Marquart-Levenberg modification of the Gauss-Newton method, and is capable of weighted multiple simultaneous curve-fitting.

The transport of leucovorin, methotrexate, and trimetrexate was investigated using standard techniques. Ten to twenty $\times 10^6$ freshly harvested intact toxoplasma trophozoites or HL-60 cells were suspended in 300 microliters of a 160 mm HEPES/2mm $MgCl_2$ solution. The organisms or cells were then exposed to various concentrations of [$^3$H]-methotrexate (sp. act. = 18 Ci/mmol), [$^3$H]-1-5-formyl-$H_4$PteGlu (sp. act. = 1.5 Ci/mmol) or [$^{14}$C]trimetrexate (sp. act. = 13.1 mCi/mmol) for specific time periods followed by centrifugation at 15,000×g for one minute through 1 ml of F50 silicon fluid (General Electric, Waterford, N.Y.) to separate the cells from the radiolabelled media. [$^3$H]-1-5-Formyl $H_4$PteGlu (Leucovorin) (sp. Act. = 1.5 Ci/mmol) was synthesized from [3',5',7,9-$^3$H]folic acid by enzymatic reduction to tetrahydrofolic acid followed by formylation and purification.

The cell pellets were then disrupted by dissolution in 500 ml of 1M NaOH followed by 10 ml of scintillant, and the cell pellets were then counted in a liquid scintillation counter. Nonspecific background counts were established for each concentration of each radiolabelled compound by adding the radiolabelled compound to the cells, then immediately quenching the transport of the radiolabelled compound by the addition of a 1000-fold excess of unlabelled compound, and proceeding as above. The transport of leucovorin and antifolates trimetrexate and methotrexate is shown in Table 2.

trexate as compared to the binding of the diaminopyrimidines.

TABLE 3

| | Comparative Inhibition of DHFR from T. Gondii by Antifolates | | | | | |
|---|---|---|---|---|---|---|
| | Human | | L. Casei | | Toxoplasma | |
| | Inhibition of Enzyme Activity $I_{50}$ ($\mu M$) | Relative Potency of Binding | Inhibition of Enzyme Activity $I_{50}$ ($\mu M$) | Relative Potency of Binding | Inhibition of Enzyme Activity $I_{50}$ ($\mu M$) | Relative Potency of Binding |
| Trimethoprim | 1300 ± 250* | 0.000033 | 0.28 ± 0.07 | 0.022 | 14.5 ± 1.9 | 0.0011 |
| Pyrimethamine | 5.8 ± 0.14 | 0.0049 | 7.4 ± 1.1 | 0.00015 | 0.76 ± 0.13 | 0.0087 |
| Trimetrexate | 0.0032 ± 0.00064 | 0.625 | 0.0061 ± 0.0011 | 0.17 | 0.0014 ± 0.00016 | 3.33 |
| Methotrexate | 0.0012 ± 0.00018 | 1 | 0.0018 ± 0.00027 | 1 | 0.021 ± 0.0029 | 1 |

*SEM

TABLE 2
TRANSPORT OF LEUCOVORIN AND ANTIFOLATES: STEADY-STATE INTRACELLULAR CONCENTRATIONS WITH 1 $\mu M$ EXPOSURES

| | Leucovorin pmoles/$10^7$ cells | Trimetrexate pmoles/$10^7$ cells | Methotrexate pmoles/$10^7$ cells |
|---|---|---|---|
| Toxoplasma | 0 | 108 ± 36.6 | 0 |
| HL60 | 16.0 ± 3.5* | 366 ± 68.5 | 10.3 ± 0.5 |

*SEM

The peritoneal macrophage model was used to illustrate the ability of the antifolates to inhibit toxoplasma replication in the intact cell. Peritoneal macrophages harvested from BALB/c mice were plated on LAb-Tek slides at a concentration of $10^6$/ml RPMI-1640 with 10% FCS at 37° C. After 24 hours, the medium was removed and 1 ml of toxoplasma at a concentration of $2 \times 10^6$/ml RPMI-1640 with 10% FCS was added to the slides. After 30 minutes the supernate was removed, the slides were washed vigorously, and 1 ml RPMI-1640 and 10% FCS plus drug were added. One and 18 hour later, the slides were stained with Diff-quick. Two hundred to 400 cells were counted and total number of vacuoles per 100 cells and mean number of toxoplasma per vacuole were calculated.

In order to investigate the antimetabolic effects of antifolates, the ability of various antifolates to inhibit DHFR from three mammalian sources (human, rat, and bovine), from *T. Gondii*, and from a bacterial source (*Lactobacillus casei*) were examined. For each inhibitor, the ability to inhibit the catalytic reaction or to compete with [$^3$H]-methotrexate for enzyme binding was determined, as shown in Table 3. Methotrexate and trimetrexate were potent inhibitors of DHFR from mammalian, bacterial, or protozoal sources ($I_{50}$=1-21 nM). In contrast, trimethoprim weakly inhibited mammalian reductase ($I_{50}$=0.39-1.3 mM) and had intermediate potency versus bacterial reductase (0.28 micromole), while pyrimethamine had relatively equivalent potency as an inhibitor of reductase form mammalian and bacterial sources (6 micromoles). Trimethoprim and pyrimethamine weakly inhibited the toxoplasma reductase with $I_{50}$'s of 14.5 and 0.76 micromoles, respectively. The IC50 for inhibition of toxoplasma DHFR by trimetrexate was almost 600-fold lower than that of pyrimethamine and 10,000-fold lower than that of trimethoprim. A comparison of the binding affinities of the various anti-folates to DHFR from *T. gondii* confirmed the markedly greater potency of trimetrexate and metho- After investigation of the capacity of leucovorin, methotrexate, and trimetrexate to cross the toxoplasma cell membrane, it was found that classical folate structures such as leucovorin (Table 2) did not penetrate the organisms. However, the uptake of trimetrexate was rapid, reaching a steady state of 108 pmoles/$10^7$ cells within ten minutes. For comparison, the uptake of these compounds was quantitated in a human leukemia cell line, HL-60. All three compounds were transported by this cell line with steady-state levels of methotrexate approximately equal to that of leucovorin, while trimetrexate levels were almost 30 times greater than either of the former compounds at an equivalent extracellular concentration. Accounting for the threefold difference in size between the tropohzoites ($32 \times 10^6$ cells/mg cytosolic protein) and HL60 ($10 \times 10^6$ cells/mg cytosolic protein), the steady-state levels of trimetrexate are equivalent from the two cell types, 324 pmoles/mg cytosolic protein in trophozoites and 36,565 pmoles/mg of cytosolic protein in HL60 cells.

Studies were also performed to assess the relative potencies of the various antifolates as inhibitors of toxoplasma replication in intact toxoplasma-infected murine peritoneal macrophages. Toxoplasma replication was 50% inhibited by a trimetrexate concentration of $10^{-8}$M and completely inhibited at concentrations in excess of $10^{-7}$M. Pyrimethamine and trimethaprim required cooncentrations of at least $10^{-6}$ and $10^{-4}$M, respectively, for equivalent activity. Methotrexate was ineffective when used at concentrations up to $10^{-4}$ M. In addition, concomitant addition of leucovorin (up to $10^{-5}$M) had no inhibitory effect on the antiprotozoal effects of the drugs but prevented toxicity to the mammalian cells.

In vivo studies were performed to demonstrate the ability of trimetrexate to increase the survival of mice infected intraperitoneally with $5 \times 10^5$ toxoplasma (RH strain). In preliminary studies, it was found that trimetrexate, 80 mg/kg/day for nine days, intraperitoneally, was 100% lethal to uninfected animals. Simultaneous treatment with the same dose of trimetrexate and an equivalent dose of leucovorin (80 mg/kg/day) for nine days produced no lethality.

In vivo studies were carried out to assess the antiprotozoal effect of trimetrexate with leucovorin. These studies used trimetrexate at a dosage of 30 mg/kg/day and leucovorin at a dose of 30 mg/kg/day for 9 days, beginning 24 hours after inoculation with organisms. This demonstrated a potent antiprotozoal effect of trimetrexate in prolonging the survival of toxoplasma-bearing mice by greater than 300%. The survival of untreated control animals (n=14) was 6.3=0.9 days compared to 20.3=1.7 days for the drug-treated animals (n=14).

It has been found that the antiprotozoal activity of trimetrexate is 600-fold more potent than the conventional antifolate, pyrimethamine, as an inhibitor of protozoal DHFR. In comparative studies of inhibitors of DHFR using enzyme derived from mammalian, protozoal, and bacterial sources, the diaminopyrimidine antifolates (trimethoprim and pyrimethamine) only weakly inhibit the protozoal and mammalian enzymes, in contrast to the pteridine and quinazoline structure, which potently inhibited the enzyme from all three sources. Bacteria possess a DHFR exquisitely sensitive to the diaminopyrimidines due to the availability of additional hydrogen bonding at Caline 115 as compared to the lack of bonding at this position in the insensitive mammalian enzyme. The combination of sulfa and a diaminopyrimidine is highly effective in treating certain bacterial infections, particularly those of the urinary tract, but the treatment of toxoplasmosis in immunosuppressed humans, particularly those with AIDS, is often unsuccessful. Many of these patients cannot tolerate such combination therapy because of allergic responses, hepatitis, or leukopenia, while others demonstrate clinically resistant infections.

In order to determine the antiprotozoal activity of trimetrexate against *Toxoplasma gondii* in mice, trimetrexate plus leucovorin was compared with no drug. For all in vivo studies, groups of female BALB/c mice (20-25 grams) were injected intraperitoneally with either drugs or toxoplasma organisms. All injections were made with 25-gauge needles, and the animals were allowed food and water ad lib. Survival was used as the primary indicator of response.

The results of the above study are summarized in Table 4.

TABLE 4

ANTIPROTOZOAL ACTIVITY OF TRIMETREXATE AGAINST TOXOPLASMA GONDII IN MICE

| Drug | Dose/Schedule | No. of Mice | Mean Day of Death | ICs (%) |
|---|---|---|---|---|
| None | — | 6 | 6.5 | — |
| Trimetrexate × Leucovorin | 30 mg/kg/d × 9 days | 6 | 14.7 | 226 |

It can be seen from the above studies that trimetrexate is a useful inhibitor of dihydrofolate reductase, both in toxoplasmosis or *P. carinii*. Because tremetrexate is lipid soluble, it also has a great capacity to enter the organisms being treated.

PC organisms were harvested from the lungs of infected rats following six weeks of oral steroid therapy. The PC DHFR was isolated as a crude cytosolic preparation free of contaminating mammalian reductase. Proof of the purity of the preparation is dependent on several lines of evidence, including the uniphasic nature of inhibition of the reductase, inhibition constants that were significantly different from those of rat DHFR, lack of detectable DHFR activity in preparations of contaminating cells (i.e., rat lung cells, yeast, rat red cells, and rat white cells), molecular weight measurements of the presumptive PC DHFR (18,000 KD) versus rat DHFR (21,000 KD), and inability to inhibit the presumptive PC DHFR by a polyclonal antibody capable of fully inhibiting the catalytic activity of rat DHFR. DHFR activity was measured in the PC cytosolic preatations, and the specific activity was found to be 4 nmols/min/g at 37° C.

The antifolates trimethoprim, pyrimethamine, methotrexate, and tremetrexate were tested as inhibitors of the reaction catalyzed by the PC DHFR as well as the rat liver DHFR. Trimethoprim, the currently used antifolate, was found to be the weakest inhibitor, requiring a concentration of 23 micromoles to inhibit the reaction by one-half. Pyrimethamine was a 10-fold more potent inhibitor, but trimetrexate was greater than 1500-fold more potent than trimethoprim, with an $I_{50}$ of 21 nM. Methotrexate, which is not transported by the PC organisms, was even more potent than trimetrexate. These relationships are similar to those of the mammalian reductase but distinct from those of bacteria and other protozoa that demonstrate an exquisite sensitivity to the diaminopyrimidines.

The relative potency of binding reflects the relative ability compared to methotrexate of each inhibitor to compete with [$^3$H]-methotrexate for binding to either rat or PC DHFR. Table 4 also illustrates an additional measurement of the ability of the antifolates to interact with the PC DHFR.

The relative potency of binding reflects the relative ability compared to methotrexate of each inhibitor to compete with [$^3$H]-methotrexate for binding to either rat or PC DHFR. These results support $I_{50}$ values generated from inhibition studies on the catalytic reaction, in that trimetrexate was found to be considerably more potent that trimethoprim and pyrimethamine, respectively, in its ability to compete with methotrexate for PC DHFR binding.

Classic folate structures such as the reduced folate leucovorin (5-formyltetrahydrofolic acid) and methotrexate require a special carrier-mediated active transport system to cross cellular membranes. This system is present on mamamlian cells, but absent in certain bacteria and protozoa, and thus precludes the use of methotrexate as a therapeutic option. For these infections, radiolabelled compounds were used to investigate the transport of leucovorin, methotrexate, and trimetrexate in intact PC organisms and a human promyelocytic cell line, HL-60, that possesses a known reduced folate transport system. Table 3 illustrates that at 1 micromole concentrations, detectable uptake of leucovorin and methotrexate was readily detected in both mammalian cells and PC organisms, with equilibrium amounts of 366 and 76 pmoles/mg of cytosolic protein, respectively.

These experiments demonstrate that PC contains a dihydrofolate reductase that can be separated and examined in the absence of contaminating mammalian reductase. The diaminopyrimidines that are potent inhibitors of bacterial and plasmodial DHFR are unexpectedly weak inhibitors of the PC DHFR, while the classic antifolate methotrexate and its lipid-soluble analog are extremely potent inhibitors of the PC reductase, with I50's of 1.4 and 26.1 nM, respectively. The $I_{50}$ of trimetrexate reflects a greater than 1500-fold increased potency of this compound when compared to trimethoprim, the current antifolate used for the treatment of PC pneumonia in humans. The transport studies indicate that the PC organisms do not posses the membrane mechanism required for the transmembrane transport of folates (leucovorin) and methotrexate, but the hydrophobic nature of trimetrexate allows ready intracellular access. These findings suggest that one reason for the clinical inadequacy of trimethoprim may be related to its weak inhibitory properties with respect to PC DHFR. Further, the organism's inability to transport leucovorin suggests that a large therapeutic:toxic ratio may be accomplished through the use of the potent PC DHFR inhibitor (trimetrexate) with specific rescue of the cells by leucovorin. Reduced folates such as leucovorin have extensively documented ability to reverse the cellular toxicity of antifolate drugs.

The potency of the interaction of various inhibitors with rat liver (sp. act. 3.7 units/mg) and *Pneumocistis carinii* DHFR was evaluated by two methods: (1) ability of the antifolates to inhibit the reaction catalyzed by the DHFR, and (2) the ability of the antifolates to compete with radiolabelled methotrexate for binding to either rat of PC DHFR.

TABLE 5

COMPARATIVE INHIBITION OF DHFR FROM *PNEUMOCYSTIS CARINII* AND RAT LIVER BY ANTIFOLATES

|  | Rat Liver Inhibition of Enzyme Activity ($I_{50}$) | Pneumocystis Carinii Inhibition of Enzyme Activity ($I_{50}$) |
|---|---|---|
| Tremethoprim (nM) | 390,000 ± 150,000 | 39,600 ± 3,800 |
| Pyrimethamine (nM) | 2,400 ± 900 | 2,800 ± 300 |
| Trimetrexate (nM) | 5.7 ± 1.1 | 26.1 ± 2.2 |
| Methotrexate (nM) | 1.4 ± 0.5 | 1.4 ± 0.2 |

The $I_{50}$ values in Table 5 represent the concentration of each inhibitor required to inhibit the reaction by 50%. PC DHFR was used as a 100,000×g sytosolic preparation of sonicated PC organisms in the presence of 50 micrograms each of the protease inhibitors leupeptin and chymostatin. The organisms were separated form contaminating mammalian cells by Ficoll-Hypaque centrifugation. The specific activity of the PC DHFR was found to be 3.9±1.6 nmole/min/mg protein at 37° C. The spectrophotometric assay was used to measure the reaction velocity. Each 1 ml assay contained 9.15 micromoles of NADPH in 60 mM Tris-HCl, pH 7.2, and 160 mM KCl with DHFR and various concentrations of inhibitor. After temperature equilibration (37° C.), the reaction was initiated by the addition of 0.075 micromoles of dihydrofolic acid, and the reaction velocity was measured by the disappearance of NADPH at 340 nM.

To measure the ability of the anitfolates to compete with radiolabelled methotrexate for binding, the relative potency of binding was calculated from the ratio of the labelled methotrexate concentration ($2\times10^{-9}M$) to the concentration of inhibitor required to displace one-half of the enzyme-bound methotrexate. Each 450 microliter assay contained 0.15 mole of NADPH, 1 pmole of [3H]-methotrexate (sp. act.=18 ci/mmol), and various concentrations of competitors (inhibitors) in 50 mM $KH_2PO_4$, pH 7.4. The competition was begun with the addition of enzyme, and following 10 minutes of equilibration at 21° C., the unbound ligand was adsorbed using acid-washed, activated charcoal, and separated by filtration as previously described. The separated, protein-bound [$^3H$]-methotrexate was then dissolved in scintillant and counted in a liquid scintillation counter. All tabulated values form both assays were calculated using ALLFIT, a least-squares curve-fitting program capable of simultaneous curve-fitting.

The uptake of radiolabelled methotrexate (sp. act. 18 Ci/mmol), trimetrexate (sp. act. 13.1 mCi/mmol), and leucovorin (sp. act. 1.5 Ci/mmol) was measured in both a human promyelooytic cell line (HL-60) and intact PC organisms. [3H]-l-5-Formyltetrahydrofolic acid (leucovorin) was prepared from [3',5',7,9-3H]-folic acid by enzymatic reduction to tetrahydrofolic acid followed by formulation and purification.

Intact HL-60 cells or PC organisms were suspended in 300 microliters of 160 nM HEPES/2 mM $MgCl_2$ at 21° C. and exposed to 1 micromole concentrations of labelled compounds for up to 30 minutes. Following the exposures, the cells/organisms were sedimented through 1 ml of F50 silicon fluid at 15,000×g for one minute. The cell pellets were dissolved in 0/5 ml of 1N NaOH and radioactivity was counted in a liquid scintiallation counter after the addition of 10 ml scintillant. Nonspecific background counts were established for each radiolabelled compound by adding the radiolabelled compound to the cells and then immediately quenching the transport of the radiolabelled compound by the addition of a 1000-fold excess of unlabelled compound followed by processing as outlined above.

It has been found that a dosing schedule of from about 10 to 50 mg/kg intraperitoneally for up to nine days has been effective in treating such infections of toxoplasmosis or *P. carinii*. Although the trimetrexate is conveniently administered intraperitoneally, it can be administered by any convenient method, such as orally, percutaneously, etc.

The foregoing description of the specific embodiment(s) will so fully reveal the general nature of the invention that others can, by applying current knowledge, readily modify and/or adapt for various applications such specific embodiment(s) without departing from the generic concept, and, therefore, such adaptations and modifications should and are intended to be comprehended within the meaning and range of equivalents of the disclosed embodiment(s). It is to be understood that the phraseology or terminology employed herein is for the purpose of description and not of limitation.

What is claimed is:

1. A method for treating infections of Toxoplasmosis or *P. carinii* comprising administering to a mammelian host in need of said treatment an amount of trimetrexate effective to treat said Toxoplasmosis or *P. carinii*.

2. The method of claim 1 wherein the trimetrexate is administered orally.

3. The method of claim 1 wherein the trimetrexate is administered in a dosage of about 30 mg/kg.

4. The method of claim 1 wherein the trimetrexate is administered in combination with leucovorin.

5. A method of inhibiting dihydrofolate reductase production by *T. gondii* or *P. carinii* in a mammalian host comprising administering to said mammalian host an amount of trimetrexate effective to inhibit said dihydrofolate reductase production.

* * * * *

UNITED STATES PATENT AND TRADEMARK OFFICE
CERTIFICATE OF CORRECTION

PATENT NO. : 4,694,007
DATED : September 15, 1987
INVENTOR(S) : ALLEGRA et al

It is certified that error appears in the above-identified patent and that said Letters Patent is hereby corrected as shown below:

Column 11, line 40, change "60" to -- 160 --.

Column 12, line 6, change "promyelooytic" to -- promyelocytic --.

Signed and Sealed this

Twenty-sixth Day of April, 1988

Attest:

DONALD J. QUIGG

*Attesting Officer*  *Commissioner of Patents and Trademarks*